US006784154B2

(12) United States Patent
Westenfelder

(10) Patent No.: US 6,784,154 B2
(45) Date of Patent: Aug. 31, 2004

(54) METHOD OF USE OF ERYTHROPOIETIN TO TREAT ISCHEMIC ACUTE RENAL FAILURE

(75) Inventor: Christof Westenfelder, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 345 days.

(21) Appl. No.: 10/003,352

(22) Filed: Nov. 1, 2001

(65) Prior Publication Data

US 2003/0083251 A1 May 1, 2003

(51) Int. Cl.$^7$ .................. A61K 38/00; C07K 14/00; C07K 14/505
(52) U.S. Cl. .................. 514/2; 514/814; 530/350; 930/90
(58) Field of Search ............... 514/2, 814; 530/350; 930/90

(56) References Cited

U.S. PATENT DOCUMENTS 6,274,158 B1   8/2001   Czeizler .................. 424/423

OTHER PUBLICATIONS

Adamson, J., et al., "Erythropoietin for End–Stage Renal Disease," The New England Journal of Medicine, vol. 339, Aug. 27, 1998, pp. 625–726.
Allgren, R., et al., "Anaritide in Acute Tubular Necrosis," The New England Journal of Medicine, vol. 336, No. 12, Mar. 20, 1997, pp. 828–834.
Allon, M., "Renal Abnormalities is Sickle Cell Disease," Arch Intern Med, vol. 150, Mar. 1990, pp. 501–504.
Bacallao, R., et al., "Molecular Events in the Organization of Renal Tubular Epithelium: From Nephrogenesis to Regeneration," American Physiological Society Editorial Review, 1989, pp. F913–F924.
Bachmann, S., et al., "Co–localization of Erthyropoietin mRNA and Ecto–5'–Nucleotidase Immunoreactivity in Pertibular Cells of Rat Renal Cortex Indicates That Fibroblasts Produce Erythropoietin," The Journal of Histrochemistry and Cytochemistry, vol. 41, No. 3, 1993, pp. 335–341.
Banerjee, D., et al., "Exposure of Endothelial Cells to Recombinant Human Erythropoietin Induces Nitric Oxide Synthase Acvitity," Kidney International vol. 57, 2000, pp. 1895–1904.
Beeri, R., et al., "Rapid DNA Fragmentation from Hypoxia Along the Thick Ascending Limb of Rat Kidneys," Kidney International, vol. 47, 1995, pp. 1806–1810.
Bonventre, J., "Pathogenetic and Regenerative Mechanisms in Acute Tubular Necrosis," Kidney Blood Press Res, 1998, vol. 21, pp. 226–229.

Bonventre, J., et al., "Acute Renal Failure. I. Relative Importance of Proximal vs. Distal Tubular Injury," American Physiological Society Acute Renal Failure Forum, 1998, pp. F623–F631.
Bonventre, J., "Mechanisms of Ischemic Acute Renal Failure," Kidney International, vol. 43, 1993, pp. 1160–1178.
Boom, H., et al., "Delayed Graft Function Influences Renal Function, But Not Survival," Kidney International, vol. 58, 2000, pp. 859–866.
Chertow, G., et al., "Independent Association Between Acute Renal Failure and Mortality Following Cardiac Surgery," The American Journal of Medicine, vol. 104, Apr. 1998, pp. 343–348.
Cohen, G., "Caspases: The Executioners of Apoposis," Biochem, vol. J., 1997, pp. 1–16.
Conger, J., "Interventions in Clinical Acute Renal Failure: What Are the Data?" American Journal of Kidney Diseases, vol. 26, No. 4, Oct. 1995, pp. 565–576.
Daemen, M., et al., "Inhibition of Apoptosis Induced by Ischemia–reperfusion Prevents Inflammation," The Journal of Clinical Investigation, vol. 104, No. 5, Sep. 1999, pp. 541–549.
Eckardt, K., et al., "Distribution of Erythropoietin Producing Cells in Rat Kidneys During Hypoxic Hypoxia," Kidney International, vol. 43, 1993, pp. 815–823.
Eschbach, J., "The Future of r–HuEPO," Nephrology Dialysis Transplantation, vol. 10, No. 2 (suppl), 1995, pp. 96–109.
Frede, S., et al., "Erythropoietin Gene Expression is Suppressed After Lipopolysaccharide or Interleukin–1B Injections in Rats," American Physiological Society, 1997, pp. R1067–R1071.
Gregoli, P., et al., "The Roles of Bcl–$X_L$ and Apopain in the Control of Erythropoiesis by Erythropoietin," Blood, vol. 90, No. 2, Jul. 15, 1997, pp. 630–640.
Gregoli, P., et al., "Function of Caspases in Regulating Apoptosis Caused by Erythropoietin Deprivation in Erythroid Progenitors," Journal of Cellular Physiology, vol. 178, 1999, pp. 133–143.

(List continued on next page.)

Primary Examiner—Christopher S. F. Low
Assistant Examiner—Holly Schnizer
(74) Attorney, Agent, or Firm—Brinks Hofer Gilson & Lione

(57) ABSTRACT

Recombinant erythropoietin is used in a method to prevent ischemic acute renal failure in patients at risk for developing ischemic acute renal failure and to treat fully-developed ischemic acute renal failure. The method is also used to prevent harmful cell apoptosis in renal tubular cells and to stimulate mitogenesis and motogenesis in renal tubular cells. The method comprises the administration of a composition of recombinant erythropoietin in a pharmacologically acceptable carrier to a patient for the purpose of preventing the development of ischemic acute renal failure, treating established acute renal failure, preventing harmful cell apoptosis in renal tubular cells.

21 Claims, 4 Drawing Sheets

OTHER PUBLICATIONS

Hammerman, M., et al., "Therapeutic Use of Growth Factors in Renal Failure," Journal of the American Society of Nephrology, vol. 5, No. 1, 1994, pp. 1–11.

Heidenreich, S., et al., "Direct Vasopressor Effect of Recombinant Human Erythropoietin on Renal Resistance Vessels," Kidney International, vol. 39, 1991, pp. 259–265.

Hirschberg, R., et al., "Multicenter Clinical Trial of Recombinant Human Insulin–like Growth Factor I In Patients with Acute Renal Failure," Kidney International, vol. 55, 1999, pp. 2423–2432.

Horiguchi, H., et al., "Cadmium and Platinum Suppression of Erythropoietin Production in Cell Culture: Clinical Implications," Blood, vol. 96, No. 12, Dec. 1, 2000, pp. 3743–2747.

Huang, C., et al., "Study of the Actions of Human Recombinant Erythropoietin on Rat Renal Haemodynamics," Clinical Science, vol. 83, 1992, pp. 453–459.

Humes, D., "Acute Renal Failure: Prevailing Challenges and Prospects for the Future," Kidney International, vol. 48, No. 50 (suppl), 1995, pp. S–26–S–32.

Jelkmann, W., "Erythropoietin: Structure, Control of Production, and Function," American Physiological Society, vol. 72, Apr. 1992, pp. 449–489.

Juul, S., et al., "Tissue Distribution of Erythropoietin and Erythropoietin Receptor in the Developing Human Fetus," Early Human Development, vol. 52, 1998, pp. 235–249.

Kartha, S., et al., "Adenine Nucleotides Stimulate Migration in Wounded Cultures of Kidney Epithelial Cells," American Society for Clinical Investigation, vol. 90, Jul. 1992, pp. 288–292.

Kelly, K., et al., "Acute Renal Failure in the New Millenium: Time to Consider Combination Therapy," Seminars in Nephrology, vol. 20, No. 1, Jan. 2000, pp. 4–19.

Koury, S., et al., "Quantitation of Erythropoietin–Producing Cells in Kidneys of Mice by In Situ Hybridization: Correlation With Hematocrit, Renal Erythropoietin mRNA, and Serum Erythropoietin Concentration," Blood, vol. 74, No. 2, Aug. 1, 1989, pp. 645–651.

Krantz, S., "Erythropoietin," Blood, vol. 77, No. 3, Feb. 1, 1991, pp. 419–434.

Kriz, W., et al., "Structural Organization of the Mammalian Kidney," The Kidney: Physiology and Pathophysiology, $2^{nd}$ Ed., 1992, pp. 707–777.

Lacombe, C., et al., "Peritubular Cells Are the Site of Erythropoietin Synthesis in the Murine Hypoxic Kidney," the American Society for Clinical Investigation, vol. 81, Feb. 1998, pp. 620–623.

Lieberthal, W., et al., "Graded ATP Depletion Can Cause Necrosis or Apoptosis of Cultured Mouse Proximal Tubular Cells," the American Physiological Society, 1998, pp. F315–F327.

Lieberthal, W., et al., "Necrosis and Apoptosis in Acute Renal Failure," Seminars in Nephrology, vol. 18, No. 5, Sep. 1998, pp. 505–518.

Maher, E., et al., "Prognosis of Critically–ill Patients with Acute Renal Failure: Apache II Score and Other Predictive Factors," Quarterly Journal of Medicine, New Series 72, No. 269, Sep. 1989, pp. 857–866.

Matas, A., et al., "Immunologic and Nonimmunologic Factors," Transplantation, vol. 69, No. 1, Jan. 15, 2000, pp. 54–58.

Maxwell, P., et al., "Identification of the Renal Erythropoietin–Producing Cells Using Transgenic Mice," Kidney International, vol. 44, 1993, pp. 1149–1162.

McWhinnie, D., et al., "Morphometric Analysis of Cellular Infiltration Assessed by Monoclonal Antibody Labeling in Sequential Human Renal Allograft Biopsies," Transplantation, vol. 42, No. 4, Oct. 1986, pp. 352–358.

Miller, S., et al., "Effects on IGF–I on Renal Function in End–Stage Chronic Renal Failure," Kidney International, vol. 46, 1994, pp. 201–207.

Molitoris, B., et al., "Cellular ATP Depletion Induces Disruption of the Spectrin Cytoskeletal Network," Veterans Affairs Research Service, 1996, pp. F790–F798.

Molitoris, B., et al., "The Role of Cell Adhesion Molecules in Ischemic Acute Renal Failure," The American Journal of Medicine, vol. 106, May 1999, pp. 583–592.

Muirhead, N., "Erythropoietin and Renal Transplantation." Kidney International, vol. 55, No. 69 (suppl), 1999, pp. S–86–S–92.

Nemoto, T., et al., "Recombinant Erythropoietin Rapidly Treats Anemia in Ischemic Acute Renal Failure," Kidney International, vol. 59, 2001, pp. 246–251.

Nielsen, O., et al., "Erythropoietin Deficiency in Acute Tubular Necrosis," Journal of Internal Medicine, vol. 227, 1990, pp. 373–380.

Nogae, S., et al., "Induction of Apoptosis in Ischemia–Reperfusion Kidney Model: Appearance of DNA Strand Breaks and Expression of FAS mRNA," Journal of American Society of Nephrology, vol. 5, 1994, pp. 905a.

Nushiro, N., et al., "Recombinant Human Erythropoietin Stimulates Tubular Reabsorption of Sodium in Anesthetized Rabbits," Hypertens Res, vol. 18, No. 3, 1995, pp. 203–207.

Ortiz, A., et al., "Apoptosis–Related Fas RNA is Expressed by Renal Cells and Increased in Renal Damage," Journal of American Society of Nephrology, vol. 4, 1993, pp. 496a.

O'Shea, M., et al., "Growth Hormone and the Kidnay: A Case Presentation and Review of the Literature," Journal of the American Society of Nephrology, vol. 3, No. 2, 1992, pp. 157–161.

O'Shea, M., et al., "Effects of IGF–1 on Renal Function in Patients with Chronic Renal Failure," the American Physiological Society, 1993, pp. F917–F922.

Prommool, S., et al., "Time Dependency of Factors Affecting Renal Alograft Survival," Journal of the American Society of Nephrology, vol. 11, 2000, pp. 565–573.

Sawyer, S. et al., "The Functional Form of the Erythropoietin Receptor is a 78–kDa Protein: Correlation with Cell Surface Expression, Endocytosis, and Phosphorylation," Proc. Natl. Acad. Sci., vol. 90, Jul. 1993, pp. 6849–6853.

Schelling, J., et al., "Fas–Dependent Fratricidal Apoptosis Is a Mechanism of Tubular Epithelial Cell Depletion in Chronic Renal Failure," Case Western Reserve University School of Medicine, Cleveland, Ohio, 1997, pp. 12.

Schumer, M., et al., "Morphologic, Biochemical and Molecular Evidence of Apoptosis During the Reperfusion Phase After Brief Periods of Renal Ischemia," American Journal of Pathology, vol. 140, No. 4, Apr. 1992, pp. 831–838.

Shimizu, A., et al., "Apoptosis and Cell Desquamation in Repair Process of Ischemic Tubular Necrosis," Virchows Archiv B Cell Pathology, vol. 64, 1993, pp. 171–180.

Siren, A., et al., "Erythropoietin Prevents Neuronal Apoptosis After Cerebral Ischemia and Metabolic Stress," PNAS, vol. 98, No. 7, Mar. 27, 2001, pp. 4044–4049.

Star, R., "Treatment of Acute Renal Failure," Kidney International, vol. 54, 1998, pp. 1817–1831.

Tan, C., et al., "Erythropoietin Production in Rats with Post–Ischemic Acute Renal Failure," Kidney International, vol. 50, 1996, pp. 1958–1964.

Toback, F., "Regeneration After Acute Tubular Necrosis," Kidney Interantional, vol. 41, 1992, pp. 226–246.

Vaziri, N., et al., "Erythropoietin Enhances Recovery from Cisplatin–Induced Acute Renal Failure," the American Physiological Society, 1994, pp. F360–F366.

Venekatachalam, M., et al., "Ischemic Damage and Repair in the Rat Proximal Tubule: Differences Among the $S_1$, $S_2$, and $S_3$, Segments." Kidney International, vol. 14, 1978, pp. 31–49.

Weinberg, J., "The Cell Biology of Ischemic Renal Injury," Kidney International, vol. 39, 1991, pp. 476–500.

Westenfelder, C., "Mitogenic and Motogenic Actions of Erythropoietin (EPO) on Tubular Cells Appear To Accelerate Functional Recovery from Ischemic Acute Renal Failure (ARF) in Rats." Journal of American Society of Nephrology, vol. 11, 2000, pp. 597a.

Westenfelder, C., et al., "Renal Tubular Function in Glycerol–Induced Acute Renal Failure," Kidney International, vol. 18, 1980, pp. 432–444.

Westenfelder, C., et al., "Anti–Apoptotic, Mitogenic and Motogenic Actions of Erthropoietin on Tubular Cells Protect Renal Function and Accelerate Recovery From Ischemic Acute Renal Failure in Rats," Kidney International, vol. 49, No. 1, Jan. 2001, pp. 319.

Westenfelder, C., et al., "Human, Rat, and Mouse Kidney Cells Express Functional Erythropoietin Receptors," Kidney International, vol. 55, 1999, pp. 808–820.

Westenfelder, C., et al., "Erythropoietin Stimulates Proliferation of Human Renal Carcinoma Cells," Kidney International, vol. 58, 2000, pp. 647–657.

Witzhall, R., et al., "Localization of Proliferating Cell Nuclear Antigen, Vimentin, c–Fos, and Clusterin in the Postischemic Kidney," Journal of Clinical Investigations, vol. 93, May 1994, pp. 2175–2188.

Wood, P., et al., "Cisplatin–Associated Anemia: An Erythropoietin Deficiency Syndrome," Journal of Clinical Investigations, vol. 95, Apr. 1995, pp. 1650–1659.

Yaoita, H., et al., "Attenuation of Ischemia/Reperfusion Injury in Rats by a Caspase Inhibitor," American Heart Association, vol. 97, 1998, pp. 276–281.

Youssoufian, H., et al., "Structure, Function, and Activaion of the Erythropoietin Receptor," Blood, vol. 81, No. 9, May 1, 1993, pp. 2223–2236.

Nemoto et al., "*Recombinant Erythropoietin Rapidly Treats Anemia in Ischemic Acute Renal Failure,*" J. Am. Soc. Nephrol. Sep. 2000, vol. 11, p. 594A, Abstract A3134.

Nemoto et al., "*Recombinant Erythropoietin Rapidly Treats Anemia in Ischemic Acute Renal Failure,*" Kidney Intl. Jan. 2001, vol. 59, pp. 246–251, especially p. 246, Col. 1, $1^{st}$ para.; p. 247, Col. 1, $1^{st}$ para.; pp. 249–250, Discussion.

Tan et al., "*Erythropoietin Production in Rats with Post–Ischemic Acute Renal Failure,*" Kidney Intl. 1996, vol. 50, pp. 1958–1964, especially abstract, p. 1963, Col. 2, last para.

Westenfelder et al., "*Erythropoietin (EPO) Treatment Ameliorates Ischemic Acute Renal Failure (ARF) in Rats by its Anti–Apoptotic, Motogenic and Mitogenic Actions,*" J. Am. Soc. Hephrol., Sep. 2001, vol. 12, Program and Abstract Issue, p. 739 A, Abstract A3857.

Westenfelder et al., "*Anti–Apoptotic, Mitogenic, and Motogenic Actions of Erythropoietin on Tubular Cells Protect Renal Function and Accelerate Recovery from Ischemica Acute Renal Failure in Rats,*" J. Ivnest. Med. Jan. 2001, vol. 49, No. 1, p. 89A, Abstract 319.

Westenfelder et al., *Mitogenic and Motogenic Actions of Erythropoietin (EPO) on Tubular Cells Appear to Accelerate Recovery from Ischemic Acute Renal Failure (ARF) in Rats,* J. Am. Soc. Nephrol Sep. 2000, vol. 11, Program and Abstract Issue, p. 597A, Abstract A3148.

Westenfelder et al., "*Unexpected Renal Actions of Erythropoietin,*" Exp. Nephrol. 2002, vol. 10, pp. 294–298, especially Abstract, p. 296, Col. 1, $3^{rd}$ para. and section (c) on pp. 296–297.

Copy of International Search Report corresponding to PCT Application PCT/US02/35164 dated Jun. 4, 2003, 3 pages.

(A)

Mouse proximal tubular cells (MCT)

2-DEOXYGLUCOSE (B)

Human proximal tubular cells (HK-2)

2-DEOXYGLUCOSE (A)

(B)

(A)

(B)

METHOD OF USE OF ERYTHROPOIETIN TO TREAT ISCHEMIC ACUTE RENAL FAILURE

STATEMENT REGARDING FEDERALLY SPONSORED RESEARCH OR DEVELOPMENT

The subject matter described herein was in-part made possible by support from the Department of Veterans Affairs, Dialysis Research Foundation, National Kidney Foundation, and The Heart, Lung and Blood Institute of the NIH. The government has certain rights in the invention.

BACKGROUND OF THE INVENTION

This invention relates to a method of use of a composition of matter. More particularly, the invention relates to a novel method of using a pharmaceutical composition comprising erythropoietin for treating ischemic acute renal failure (ARF) and for preventing the onset of ischemic ARF.

Clinical acute renal failure (ARF) remains a common and serious complication associated with high morbidity and mortality. Moderately effective measures to prevent ARF include volume expansion, and in renal transplants, mannitol administration. The uremic state, volume and electrolyte disturbances can be readily corrected by hemodialysis, and outcomes are improved when more biocompatible dialysis membranes are used. In addition, administration of atrial natriuretic peptide has been found to speed the improvement of renal function in some patients with ARF.

In the induction phase of ARF, cell necrosis, apoptosis, and sub-lethal injury are observed [1,2,3,4,5,6]. These effects are thought to collectively contribute to the loss of renal function via pathological activation of tubuloglomerular feedback, back leak of ultrafiltrate, tubular obstruction and ineffective transport by partially depolarized tubular cells [1,2,3,4,5,6]. In the repair phase of ARF, reepithelialization of injured tubules is accomplished by migration of cells ("motogenesis") into deepithelialized nephron segments, cell proliferation ("mitogenesis"), and redifferentiation of newly generated and sublethally injured tubular cells [1,6,7]. Anabolic mechanisms and improvement of intrarenal hemodynamics are also critical to functional recovery [1,2,8,9,10].

A number of growth factors, including IGF-I, EGF and HGF, and atrial natriuretic peptide have been shown to improve renal outcome in animals with experimental ARF by modulation of the cellular and hemodynamic responses that are characteristic in ARF [8,9,10]. However, neither IGF-I nor atrial natriuretic peptide has been found to improve outcomes in patients with ARF [11,12]. Thus, successful treatment of experimental ARF in animal models is not indicative of success in humans.

EPO controls erythropoiesis by receptor-mediated regulation of survival, proliferation, and differentiation of erythroid progenitor cells [13,14]. In adult mammals, erythropoietin (EPO) is primarily produced by type-I interstitial cells of the juxtamedullary renal cortical labyrinth [13,14,15,16,17]. Renal and hepatic EPO synthesis and release are increased when intrarenal or hepatic tissue oxygenation is decreased. Renal EPO secretion occurs first into peritubular capillary blood that contains residual EPO and that reaches a large number of renal cells before delivering the hormone, via renal veins, into the systemic circulation. Intriguingly, EPO-producing cells are also in direct contact with basal aspects of proximal and distal tubular cells [15,16,17,18,19,20]. The anatomical relationships that exist between EPO secreting cells, the intrarenal capillary network, and the tubular and other renal cells, may serve therefore to facilitate endocrine and paracrine actions of EPO within the kidney itself. It has recently been reported that authentic, mitogenically active EPO receptors (EPORs) are present in both proximal and distal renal tubular cells [21]. Since these tubular cells express EPORs, endocrine actions can be elicited.

As described previously, specific EPOR mRNAs have been shown to be expressed in the cortex, medulla and papilla of both human and rat kidneys, and EPOR protein has been identified in mouse and human proximal tubular cells [21]. Activation of EPORs in mouse proximal tubular cells by EPO was shown to stimulate DNA synthesis and cell proliferation in vitro, but the specific effect of EPO has not been described in vivo.

EPO has been described in the past as an effective treatment for cis-platinum induced ARF in rats. This form of ARF was induced by the administration of cis-platinum, a chemotherapeutic agent, and while it shows that EPO has an effect on recovery of kidney function, it does not address the more common and more serious clinical form of ARF caused by ischemia. The study also did not describe the underlying cellular and molecular effects of EPO on the renal tubular cells and provided no information regarding the expression of EPORs in renal cells [22]. In another study, EPO was administered intravenously in suprapharmacologic doses (500 to 3000 U/kg body weight) and improved hematocrits of rats with uninephrectomy and contralateral ischemic ARF, but had no effect on renal function, it increased, however animal survival by an unknown mechanism [23].

The use of EPO has also been disclosed in the past as a method to reduce excessive bleeding in patients in need thereof, such as an individual with a gunshot wound. U.S. Pat. No. 6,274,158 describes the administration of EPO in order to thicken the blood. Blood thickens as a result of EPO's effect of increasing production of red blood cells. At the high dosage levels necessary to produce the blood-thickening effect, EPO's helpful renoprotective functions are not produced.

Due to the high mortality and morbidity among individuals with ischemic ARF, a novel treatment strategy for both protecting against the onset of ischemic ARF and for treating individuals suffering from ischemic ARF would be a significant advancement in the art.

BRIEF SUMMARY OF THE INVENTION

The present invention provides a method of preventing the onset of ischemic ARF in an individual by administration of a composition of EPO in a pharmaceutically acceptable carrier.

The present invention also provides a method for treating an individual suffering from ischemic ARF by administration of a composition of EPO in a pharmaceutically acceptable carrier.

The present invention also provides a method for preventing potentially harmful cell apoptosis in renal tubular cells by administration of a composition of EPO in a pharmaceutically acceptable carrier.

The present invention also provides a method for stimulating motogenesis and mitogenesis in renal tubular cells by administration of a composition of EPO in a pharmaceutically acceptable carrier.

Preferably, the EPO is recombinant or naturally-derived EPO, and the composition is administered systemically such that the EPO circulates through the body. The composition can further comprise other ingredients such as pharmaceutically acceptable solvents, diluents, excipients, emulsifiers, stabilizers, and mixtures thereof.

BRIEF DESCRIPTION OF THE SEVERAL VIEWS OF THE DRAWINGS

FIG. 1A shows the results measured by thymidine incorporation and FIG. 1B shows the results measured by MTT assay. FIG. 1C shows the results of EPO and 10% NCS on mitogenesis and FIG. 1D shows a comparison of the mitogenic effects of EPO and NCS.

FIG. 3A shows the results at 24 hours and FIG. 3B shows the results at 48 hours.

DETAILED DESCRIPTION

Figure 1:
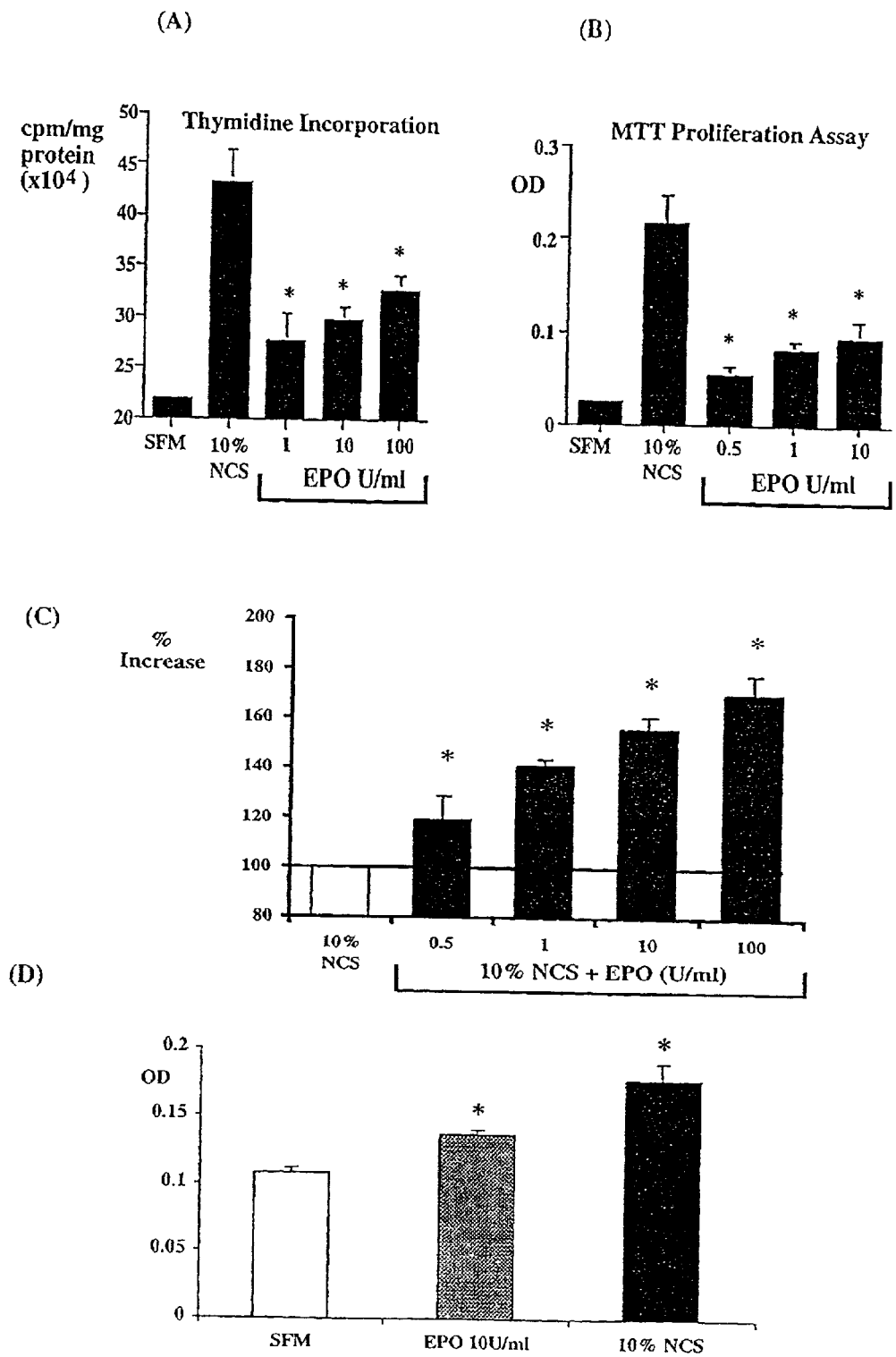
FIGS. 1A, 1B, 1C and 1D show representations of the results of experiments to measure the mitogenic effect of EPO on MCT and HK-2 cells.

The present invention stems from the discovery that EPO is a multifunctional renotropic cytokine, the actions of which are diminished in cases of ischemic ARF. Ischemic ARF causes reduced expression of EPO which in turn slows cellular recovery. The administration of EPO at subpolycythemic levels, as described in the present invention, can enhance and speed recovery from ischemic ARF without certain harmful side effects such as polycythemia, hypertension and thromboembolism.

The present invention provides a method of treating and preventing ischemia-induced ARF, or ischemic ARF. The present invention also provides a method of preventing likely harmful cell apoptosis in renal tubular cells as well as a method of stimulating mitogenesis and motogenesis in renal tubular cells. The preferred method of the present invention comprises the administration of a composition of preferably 300 U/kg body weight EPO in a carrier to an individual with ischemic ARF. The dose is preferably administered 2–4 times over a time period of 2–4 days, giving one dose every 24 hours subcutaneously or intravenously.

Before the present methods of preventing and treating ischemic ARF, preventing likely harmful cell apoptosis in renal tubular cells, and stimulating motogenesis and mitogenesis in renal tubular cells are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to "a carrier" includes reference to one or more of such carriers and reference to "an excipient" includes reference to a mixture of two or more excipients.

In describing and claiming the present invention, the following terminology will be used in accordance with the definitions set out below.

The following abbreviations are used herein: ARF, acute renal failure; EPO, erythropoietin; EPOR, erythropoietin receptor; MCT, murine proximal tubular cells; HK-2, human proximal tubular cells; BSC-1, green monkey proximal tubular cells. The abbreviation "U" stands for "units of activity," and is defined by the supplier of the recombinant EPO. In this case, the recombinant EPO used was highly pure EPOGEN™ from Amgen. The sequence of the recombinant EPO is available in GenBank at accession number XM_011627 (National Center for Biotechnology Information, Bethesda, Md.).

As used herein, "pharmaceutically acceptable" means a component that is suitable for use with humans and/or animals without undue adverse side effects (such as toxicity, irritation, and allergic response) commensurate with a reasonable benefit/risk ratio.

As used herein, "therapeutically effective amount" means an amount of EPO that is nontoxic but sufficient to provide the desired effect and performance at a reasonable benefit/risk ratio attending any medical treatment.

As used herein, "administering" and similar terms mean delivering the composition to the individual being treated such that the composition is capable of being circulated systemically to the kidney where the EPO can bind its specific receptor in the kidney. Thus, the composition is preferably administered to the individual by systemic administration, typically by subcutaneous, intramuscular, or intravenous administration, or intraperitoneal administration. Injectables for such use can be prepared in conventional forms, either as a liquid solution or suspension or in a solid form suitable for preparation as a solution or suspension in a liquid prior to injection, or as an emulsion. Suitable carriers include, for example, water, saline, dextrose, glycerol, ethanol, and the like; and if desired, minor amounts of auxiliary substances such as wetting or emulsifying agents, buffers, and the like can be added.

Ischemia is defined as a poor supply of blood to an organ. When the blood supply to the kidneys is cut off or reduced, ischemic ARF can develop. Ischemia has many causes such as multiple bodily injuries, infections invading the bloodstream (septicemia), internal or external hemorrhaging, loss of fluid from the body as a result of severe diarrhea or burns, reactions to transfusions, severe heart attacks, and kidney transplantations, as well as other surgical shock. In these situations, the blood flow to the kidneys may be reduced to dangerously low levels for a time period great enough to cause the development of ischemic ARF.

ARF occurs when renal function suddenly declines to levels so low that little or no urine is formed, and substances that the kidney usually eliminates remain in the body. Ischemia causes ARF by depressing the blood flow to the kidneys, which leads to inefficient excretion. The depressed blood flow also results in necrosis, or tissue death, in the kidney, damaging the renal tubular cells. Repair or prevention of this damage helps ameliorate ARF.

The regeneration of renal tubular cells likely depends, at least in part, on the intrinsic actions of EPO, but in ischemic ARF, the levels of EPO are also reduced, compounding the injury and preventing the regeneration of renal tubular cells.

The disclosed methods provide levels of EPO high enough to aid in the regeneration of renal tubular cells, but not so high as to cause renal vasoconstriction and other unwanted side effects, such as hypertension and thromboembolism.

The present method also helps prevent likely harmful apoptosis, or programmed cell death of tubular cells. Apoptosis of renal tubular cells is increasingly recognized as a significant mechanism that contributes to the deterioration of renal function in ARF. The administration of EPO reduces the levels of harmful apoptosis of renal tubular cells during the development and later stages of ARF. The present method of administration of EPO to patients at risk of developing ischemic ARF or with ischemic ARF also stimulates mitogenesis and motogenesis in renal tubular cells. Mitogenesis is the production of cells and motogenesis is the movement of cells to specific locations in the body. These effects result in the proliferation of new renal tubular cells and the functional recovery of an ARF-damaged kidney.

The preferred method of the present invention is ideal for the management of patients with ischemic ARF. The effects of EPO when administered according to the preferred method help ameliorate ischemic ARF and facilitate renal tubular cell repair. EPO, with its extremely high safety profile, is of particular utility in the prevention of ischemic ARF in the large number of patients who are at risk for this complication. This includes patients with diabetes mellitus, patients with underlying renal insufficiency or with nephrotic syndrome, old age, patients with atherosclerotic disease, patients who are given nephrotoxic agents (radio contrast media, aminoglycosides, cis-platinum, cyclosporin A, FK506) or patients who are septic, hypotensive, hypoxic, who undergo surgery (aortic aneurysm, cardiac repair), or who have myoglobinuria-hematuria, pregnancy associated ARF, or significant liver disease, and so forth.

The preferred embodiment of the claimed methods comprises the administration of a pharmaceutical composition containing recombinant EPO to a patient at risk for or with fully-developed ischemic ARF. The preferred pharmaceutical composition contains recombinant EPO and a pharmaceutically acceptable carrier. A "pharmaceutically acceptable carrier" includes any and all solvents, dispersion media, coatings, antibacterial and antifungal agents, isotonic and absorption delaying agents, and the like, compatible with pharmaceutical administration [24]. Preferred examples of such carriers or diluents include, but are not limited to, water, saline, finger's solutions, dextrose solution, and 5% human serum albumin. Liposomes and non-aqueous vehicles such as fixed oils may also be used. Except when a conventional media or agent is incompatible with an active compound, use of these compositions is contemplated. Supplementary active compounds can also be incorporated into the compositions.

A pharmaceutical composition is formulated to be compatible with the intended route of administration, including intravenous, intraperitoneal, intradermal, subcutaneous, transdermal (i.e., topical), and transmucosal administration. Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

Pharmaceutical compositions suitable for injection include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. The carrier can be a solvent or dispersion medium containing, for example, water, ethanol, polyol (such as glycerol, propylene glycol, and liquid polyethylene glycol), and suitable mixtures. Proper fluidity can be maintained, for example, by using a coating such as lecithin, by maintaining the required particle size in the case of dispersion and by using surfactants. Various antibacterial and antifungal agents, such as parabens, chlorobutanol, phenol, ascorbic acid, and thimerosal, can control microorganism contamination. Isotonic agents, such as sugars, polyalcohols such as manitol, sorbitol, and sodium chloride can be included in the composition. Compositions that delay absorption include agents such as aluminum monostearate and gelatin.

Sterile injectable solutions can be prepared by incorporating the active compound in an appropriate solvent with one or a combination of ingredients, followed by sterilization. Generally, dispersions are prepared by incorporating the active compound into a sterile vehicle that contains a basic dispersion medium, and any other required ingredients. Sterile powders for the preparation of sterile injectable solutions methods of preparation include vacuum drying and freeze-drying that yield a powder containing the active ingredient and any desired ingredient from a sterile solution.

Systemic administration can also be transmucosal or transdermal. For transmucosal or transdermal administration, penetrants that can permeate the target barrier(s) are selected. Transmucosal penetrants include, detergents, bile salts, and fusidic acid derivatives. Nasal sprays or suppositories can be used for transmucosal administration. For transdermal administration, the active compounds are formulated into ointments, salves, gels, or creams.

The preferred dosage of the pharmaceutical composition of the present invention comprises the administration of a subpolycythemic dose of EPO administered subcutaneously to patients at risk for, or exhibiting the symptoms of, ischemic ARF. A subpolycythemic dose is about 250–350 U/kg body weight, preferably 300 U/kg body weight. The preferred dosage of EPO prevents the development of polycythemia, a condition where there are too many red blood cells present. Polycythemia formally exists when the hemoglobin level, red blood cell count, and total red blood cell volume are all above normal, resulting in a high hematocrit level. Polycythemia results in thickened blood and retarded blood flow, and increases the danger of blood clot formation within the circulatory system. Administration of EPO at greater than subpolycythemic doses causes polycythemia as well as other negative reactions, such as renal vasoconstriction, hypertension and thromboembolism.

By utilizing a subpolycythemic dosage of EPO, such as 300 U/kg body weight, as described in the following examples, such renal vasoconstriction can be avoided and EPO's numerous renoprotective effects can occur. The recommended short-term treatment of patients with established ischemic ARF or who are at risk for developing ischemic ARF is a course of 2–4 doses at subpolycythemic concentrations. This protocol avoids adverse side effects such as thromboembolism, hypertension, and polycythemia.

In patients at risk for developing ischemic ARF, such as patients entering surgery, the preferred treatment protocol includes administering a dose of between 250–350 U/kg body weight of EPO in a pharmacological composition up to six hours prior to the ischemic ARF-inducing event. Thereafter, the preferred protocol includes administering a dose of between 250–350 U/kg body weight of EPO in a pharmacological composition 24 hours after the first dose, and thereafter every 24 hours for up to three additional daily doses. The total number of doses should not exceed four.

In patients with established ischemic ARF, the preferred treatment protocol includes administering a dose of between 250–350 U/kg body weight of EPO in a pharmacological composition. This dose is preferably repeated every 24 hours for no more than four doses.

It will be understood, however, that the specific dose level and frequency of dosage for any particular patient may be varied and depends upon a variety of factors, including the activity of the specific compound employed, the metabolic stability and length of action of that compound, the age, body weight, general health, sex, diet, mode and time of administration, rate of excretion, drug combination, the severity of the particular condition, and the host undergoing therapy.

The results in the following examples demonstrate the role of EPO in the biology of normal and injured renal cells. It is specifically shown that EPO acts as a renotropic cytokine in that it stimulates, via its receptors, tubular cell migration, DNA synthesis, and cell proliferation, all of which are essential to parenchymal repair and subsequent recovery in ischemic ARF. It has also been shown that EPO has significant anti-apoptotic effects on cells expressing EPORs. These data have elucidated many of the mechanisms that explain EPO's renoprotective actions observed in acute renal failure.

The examples presented below describe the results of recombinant EPO treatments on rats with ischemic ARF. EPO has been shown to act through its effects on EPORs in the kidney [21]. Since both rat and human kidney cells express functional EPORs, it follows that EPO will have the same effects in humans as in rat models.

It must be emphasized that the beneficial effects of EPO in ischemic ARF are not related to its effect on raising the hematocrit, but are due to its receptor-mediated actions on renal tubular and other cells. Prevention of ischemic ARF will lead to a very substantial cost savings, since the need for acute hemodialysis would be eliminated or reduced, and the many complications of ischemic ARF (uremic bleeding, hyperkalemia, acidosis, pericarditis, arrythmias, neurological complications) and those of hemodialysis per se would be ameliorated or avoided. The utility of EPO as an agent that can hasten the recovery from ischemic ARF is equally significant. It will shorten or avert the dependency on acute hemodialysis with its attendant complications and high costs.

EPO is a clinically well established hormone. Short term side effects are negligible, although higher doses have been shown to cause hypertension in about 25% of chronic dialysis patients, but not in patients with preserved renal function. An increased incidence of thrombosis has also been reported in some chronic dialysis patients, but no such side effects are seen in patients with normal renal function.

It has been noted that it has been demonstrated previously that EPO accelerates functional recovery in rats with cis-platinum-induced ARF [22]. A mitogenic response was detected, but other cytokine reactions and EPOR expression were not examined. It was shown that EPO prevents anemia in these cases, thus allowing tubular cells to heal. It was not shown that EPO directly facilitates the functional recovery of the renal tubular cells.

The EPO used in the following examples was a highly pure, recombinant EPO called EPOGEN™. (Amgen, Thousand Oaks, Calif.). This preparation is commonly used to treat human subjects.

EXAMPLE 1

The following example demonstrates the mitogenic effect of EPO on quiescent MCT and HK-2 cells. Proximal tubular cell lines of MCT and HK-2 were grown to subconfluence, rendered quiescent for 24 hours (serum free media), and then exposed to incremental concentrations of EPO (1–100 U/mL) or 10% NCS as a positive control. Mitogenic response was measured by MTT assay and in some experiments by [$^3$H] thymidine incorporation. In separate experiments, in order to asses whether EPO and NCS would have additive mitogenic effects, incremental doses of EPO (1, 5, 10 U/mL) were added to EPO-free 10% NCS.

FIG. 1 shows the data confirming that EPO alone stimulates significantly and dose-dependently cell proliferation of quiescent MCT (panels A and B) and HK-2 cells (panel D). When EPO was combined with 10% NCS, a further, dose-dependent increase in the proliferative response of MCT was observed (panel C). The possibility that this additive effect was caused by EPO in the calf serum was excluded since the endogenous EPO levels in the utilized NCS were undetectable by EIA (<10 mU/ml). These data show that the activation of EPORs on proximal tubular cells by EPO stimulates mitogenesis in tubular cells.

EXAMPLE 2

In this example, predominant apoptosis and necrosis were induced to test the anti-apoptotic effects of EPO. Cultured proximal tubular cells, HK-2 and MCT, were subjected to chemical ATP depletion by incubation with 2-Deoxyglucose (2-DOG, 5 mM×24 hrs in glucose-free media). This insult resulted in ~50–75% ATP depletion, assessed with the Luciferin-Luciferase assay (ATP Bioluminescence Assay Kit HS II, Roche Diagnostics Corp., Indianapolis, Ind.). After 24 hours, cultures were rinsed free of 2-DOG and standard media were added for another 24 hours, either with or without the addition of recombinant human EPO (10 U/mL). Surviving cell numbers were determined by MTT assay (Thiazolyl blue, Sigma, St. Louis, Mo.).

Surviving cells were examined for the presence and percentages of apoptotic cell numbers after staining with Hoechst 33342. Cells were considered to exhibit morphologic changes indicative of apoptosis when, under immunofluorescence, definite nuclear condensation, cell shrinkage, nuclear fragmentation and apoptotic bodies were identified [3,4,25]. A calibrated eye piece (magnification× 100) and graticule grid (25 squares) were utilized to determine the percentage of apoptotic cells versus normal-appearing and necrotic cells by counting a total of 500 nuclei per culture.

Figure 2:
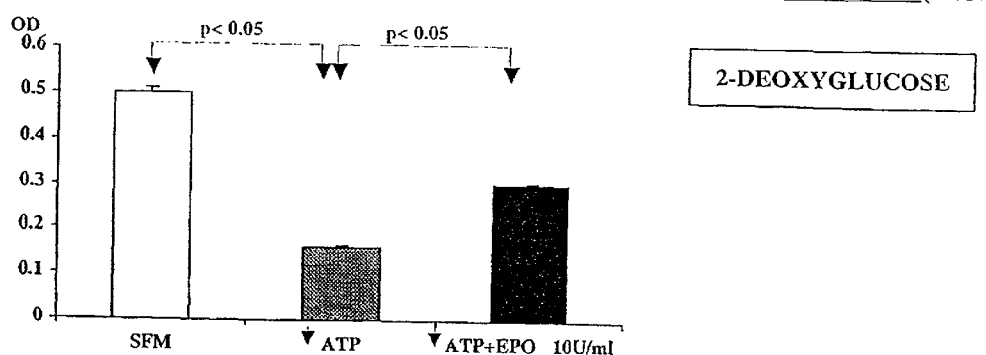
FIGS. 2A and 2B show representations of the results of experiments to measure the anti-apoptotic effects of EPO when added to ATP-depleted MCT cells (FIG. 2A) and HK-2 cells (FIG. 2B).
Figure 2:
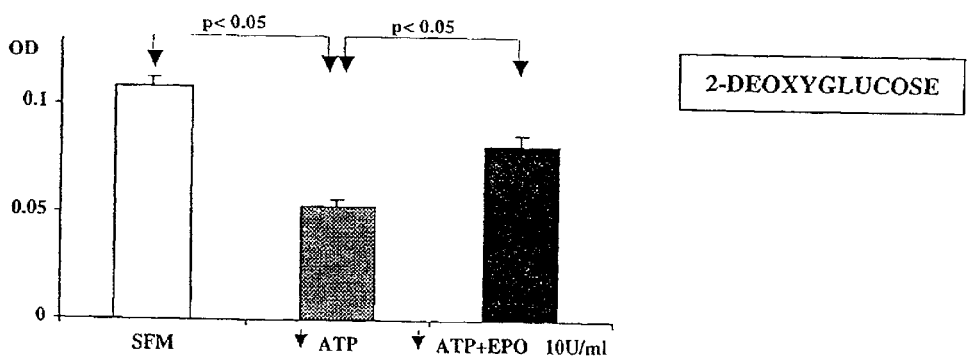

FIG. 2 depicts the data from the above experiments. Survival of cultured proximal tubular cells injured by chemical ATP depletion was significantly enhanced when 10 U/mL of EPO was added to the media. Panel A shows the data for MCT cells and panel B shows the data for HK-2 cells.

The Hoechst staining illustrated that EPO's survival-enhancing effects in ATP-depleted HK-2 cells correlates with a reduction in apoptotic cell morphology. ATP-depletion of HK-2 cells in the absence of EPO results in the appearance of numerous cells with apoptotic morphology. EPO addition reduces the number of cells displaying such apoptotic morphology.

These data demonstrate that EPO elicits significant anti-apoptotic effects in EPOR-expressing proximal tubular cells. These anti-apoptotic effects aid in the prevention of renal tubular cell damage caused by ischemia. This helps prevent the development and promote recovery from ischemic ARF.

EXAMPLE 3

In order to demonstrate the motogenic effects of EPO, BSC-1 cells were grown in monolayers and defined scrape wounds were made with a sterile pipette tip [26]. After wounding, EPO was added to the media at submitogenic concentrations (5–30 mU/mL), or for a positive control, 0.2 M ADP was added to the media. The number of cells migrating into the scrape wounds were counted at 24 and 48 hours after injury using an eye piece and a graticule grid, as in the previous example.

Figure 3:
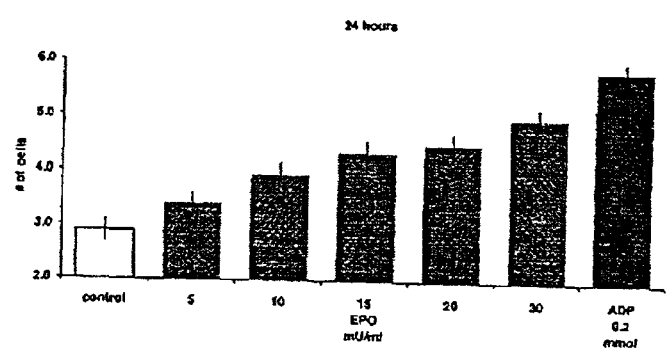
FIGS. 3A and 3B show representations of results of experiments to measure the motogenic effects of EPO on wounded monolayers of BSC-1 cells.
Figure 3:
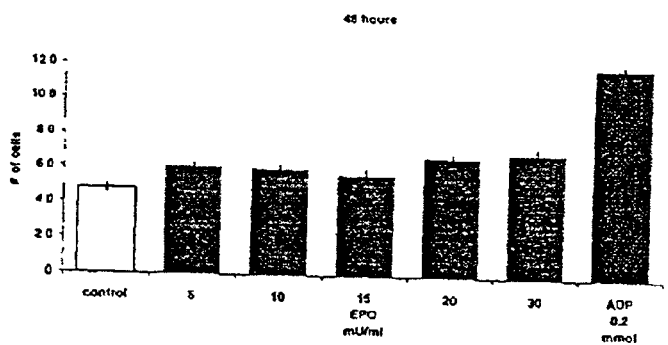

FIG. 3 shows the results of the experiment. It was demonstrated that the addition of EPO to the media in physiologic concentrations stimulates migration of BSC-1 cells into areas that had been scrape-wounded. This action was dose-dependant. The highest EPO dose stimulated cell migration to ~75% of that obtained with ADP.

These data demonstrate that EPO elicits significant motogenic effects in EPOR-expressing proximal tubular cells. These motogenic effects of EPO aid in the repair of the kidneys and recovery from ischemic ARF.

EXAMPLE 4

Normal adult, male Sprague-Dawley rats weighing 350–450 g and eating normal rat chow with free access to water were used in the following example to determine the effects of EPO on ischemic ARF. Animal weights were measured daily, and hematocrits and renal function were determined daily in tail vein blood.

Ischemic ARF was induced in groups of EPO and vehicle-treated rats. To induce ischemic ARF, the animals were anesthetized (ketamine, 90 mg/kg and xylazine 10 mg/kg injected intraperitoneally), the abdominal cavity was opened under sterile conditions and both renal pedicles were isolated and clamped with atraumatic vascular clamps for 35 or 55 minutes. Reflow after clamp release was visually confirmed prior to abdominal closure. Sham rats were identically handled except that the renal pedicles were not clamped.

EPO and EPOR expression in sham and ARF kidney cortices from 4 animals each (35 minutes of bilateral renal pedicle clamping or sham surgery) was determined at 24 hours post-reflow by anesthetizing the animals as previously described, excising the kidneys and placing them in ice cold PBS. Cortical tissue was obtained by dissection. Total RNA was extracted as described in [21]. Previously reported primer pairs were used to determine EPO and EPOR mRNA expression by RT-PCR. Generated PCR products were identified on ethidium bromide-stained agarose gels, and beta-actin served as internal control.

Ischemic ARF abolished the renal expression of EPO at 24 hours following reflow compared to control, while EPOR and beta-actin expression remained unaltered. EPOR protein expression in ischemic ARF kidneys was maintained at control levels. These results demonstrate that ischemic ARF causes EPO deficiency.

EXAMPLE 5

In the same cortical kidney tissue as the previous example, EPO and EPOR proteins were identified using an EPO ELISA (ALPCO, Windham N.H.) and Western blotting for the EPOR in tissue lysates antibody from Santa Cruz Biotechnology respectively.

Two different treatment protocols were followed. In the first, the pre-treatment group, EPO was first administered before the onset of ischemic ARF. In the second, the post-ischemic ARF group, EPO was administered for the first time after the inducement of ischemic ARF. In the pre-treatment ischemic ARF group, EPO (300 U/kg body weight), was given sub-cutaneously 6 hours prior to renal clamping, and again at 24, 48 and 72 hours after reflow. In the post-ischemic ARF group, EPO (300 U/kg body weight) was first given sub-cutaneously 24 hours after 55 minutes of renal ischemia, and again at 48 and 72 hours.

Figure 4:
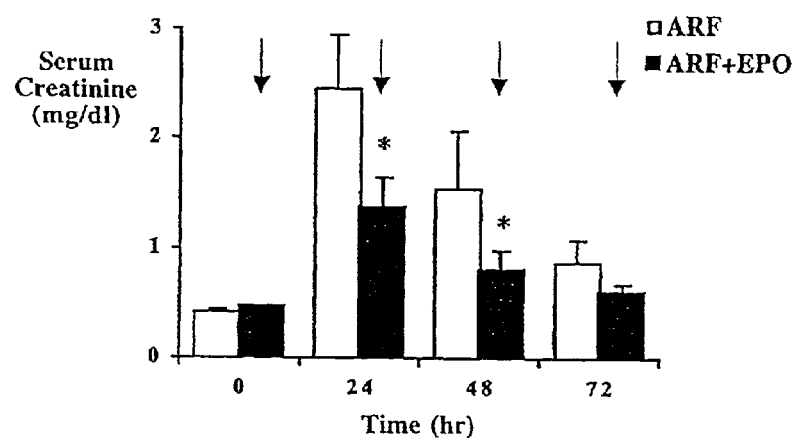
FIGS. 4A and 4B show representations of the results of an EPO pre-ARF treatment protocol (FIG. 4A) and an EPO post-ARF treatment protocol (FIG. 4B).
Figure 4:
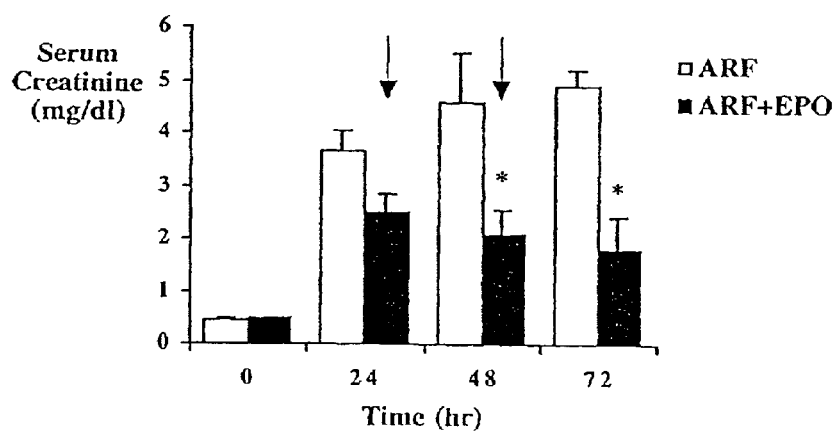

Panel A of FIG. 4 illustrates that prophylactic administration of EPO, followed by daily injections, both ameliorated the loss in renal function (assessed by serum creatinine levels) and accelerated functional recovery. Panel B shows that EPO, when first administered 24 hours following 55 minutes of bilateral ischemia, reversed functional deterioration and eliminated the 40% mortality observed in vehicle-treated ischemic ARF animals.

These data demonstrate that EPO's cytokine actions are renoprotective by ameliorating cell injury and by stimulating regeneration and functional recovery. The levels of EPO used in this experiment demonstrate a preferred protocol for use in patients both at risk for the development of ischemic ARF and with fully-developed ischemic ARF.

EXAMPLE 6

In this example, 4 vehicle treated animals with ischemic ARF, 4 EPO treated animals with ischemic ARF and 4 sham animals were treated according to the pre-treatment protocol as previously described, and were anesthetized at 48 hours following reperfusion. Blood was sampled for creatinine and kidneys were removed, rinsed free of blood with ice cold PBS and a whole cortical section (approximately 4–5 mm) was removed, placed in formalin and embedded in paraffin. Five $\mu$m sections were cut and stained with HE as described in the art [27]. Tubular necrosis was determined semiquantitatively according to a published method [28]. A ×20 objective lens and graticule with 25 squares were used to examine random areas of the renal cortex for line intersects showing tubular profiles. One hundred intersections were examined for each kidney, and a score of 0 to 3 was given for each tubular profile involving an intersection (0=normal histology, 1=tubular swelling, brush border loss, nuclear condensation, with up to 33% of the tubular profile showing nuclear loss, 2=same as score 1, but >33% and <66% of the tubular profile showing nuclear loss, 3=>66% of the tubular profile showing nuclear loss). The total score for each kidney was calculated by adding all 100 scores, making the maximum possible injury score 300.

Micrographs of rat kidney cortex at 48 hours following reflow demonstrated the histologic effects of EPO on the kidney. The kidney from the EPO treated animal showed relatively intact tubules, while the non-EPO treated kidney showed significant tubular damage consisting of extensive tubular necrosis affecting primarily proximal tubular segments. The semiquantitative injury score described above at 48 hours after reflow was significantly lower in EPO treated vs. vehicle-treated ARF animals.

These data demonstrate that EPO treatment has significant effects on the repair of proximal tubular cells in the kidneys, thus aiding in recovery from ischemic ARF.

References

1. Bonventre J: Mechanisms of ischemic renal failure. *Kidney Int* 43:1160–1178, 1993
2. Weinberg J: The cell biology of ischemic renal injury. *Kidney Int* 39:476–500, 1991
3. Schumer M et al.: Morphologic, biochemical and molecular evidence of apoptosis during the reperfusion phase after brief periods of renal ischaemia. *Am J Pathol* 140:831–838, 1992
4. Shimizu A, Yamanaka N: Apoptosis and cell desquamation in repair process of ischemic tubular necrosis. *Virchows Arch B Cell Pathol* 64:171–180, 1993
5. Witzgall R et al.: Localization of proliferating cell nuclear antigen, vimentin, c-fos, and clusterin in the postischemic kidney. Evidence for a heterogenous genetic response among nephron segments, and a large pool of mitotically active dedifferentiated cells. *J Clin Invest* 93L2175–2188, 1994
6. Molitoris B A, Marrs J: The role of cell adhesion molecules in ischemic renal failure. *Am J Med* 106:583–592, 1999
7. Toback F G: Regeneration after acute tubular necrosis. *Kidney Int* 41:226–246, 1992
8. Hammerman M, Miller S: Therapeutic use of growth factors in renal failure. *J Am Soc Nephrol* 5:1–11, 1994
9. Humes H: Acute renal failure: Prevailing challenges and prospects for the future. *Kidney Int* 50:S26–S32, 1995
10. Kelly K J, Molitoris B A: Acute renal failure in the new millennium: time to consider combination therapy. *Semin Nephrol* 20:4–19, 2000
11. Hirschberg R et al.: Multicenter clinical trial of recombinant human insulin-like growth factor I in patients with acute renal failure. *Kidney Int* 55:2423–2432, 1999
12. Allgren R L et al.: Anartide in acute tubular necrosis. Auriculin Anartide Acute Renal Failure Study Group. *N Engl J Med* 336:828–834, 1997
13. Krantz S: Erythropoietin. *Blood* 77:419–434, 1991
14. Jelkmann W: Erythropoietin: Structure, control of production, and function. *Physiol Rev* 72:449–489, 1992
15. Lacombe C et al.: Peritubular cells are the site of erythropoietin synthesis in the murine hypoxic kidney. *J Clin Invest* 81:602–623, 1988
16. Koury S et al.: Quantitation of erythropoietin-producing cells in kidneys of mice by in situ hybridization: Correlation with hematocrit, renal erythropoietin mRNA, and serum erythropoietin concentration. *Blood* 74:645–651, 1989
17. Bachmann S et al.: Co-localization of erythropoietin mRNA and ecto-5'-nucleotidase immumoreactivity in peritubular cells of rat renal cortex indicates that fibroblasts produce erythropoietin. *J. Histochem Cytochem* 41:335–341, 1993
18. Maxwell P H et al.: Identification of the renal erythropoietin-producing cells using transgenic mice. *Kidney Int* 44:1149–1162, 1993
19. Eckardt K et al.: Distribution of erythropoietin producing cells in rat kidneys during hypoxic hypoxia. *Kidney Int* 42:815–823, 1993
20. Kriz W, Kaissling B: Structural Organization of the Mammalian Kidney in The Kidney 1:707–777 (D. W. Delsin & G. Giebisch, eds. (1992).
21. Westenfelder C et al.: Human, rat and mouse kidney cells express functional erythropoietin receptors. *Kidney Int* 55:808–820, 1999
22. Vaziri N et al.: Erythropoietin enhances recovery from cisplatin-induced acute renal failure. *Am J Physiol* 266:F360–F366, 1994
23. Nemoto T et al.: Recombinant erythropoietin rapidly treats anemia in ischemic acute renal failure. *Kid. Int* 59:246–251, 2001
24. Gennaro A R: The science and practice of pharmacy. Lippincott, Williams & Wilkins, Philadelphia, Pa.
25. Lieberthal W et al.: Necrosis and apoptosis in acute renal failure. *Semin Nephrol* 18:505–518, 1998
26. Kartha S, Toback F G: Adenine nucleotides stimulate migration in wounded cultures of kidney epithelial cells. *J Clin Invest* 90:288–292, 1992
27. Westenfelder C et al.: Renal tubular function in glycerol-induced acute renal failure. *Kidney Int* 118:432–444, 1980
28. McWhinnie D L et al.: Morphometric analysis of cellular infiltration assessed by monoclonal antibody labeling in sequential human renal allograft biopsies. *Transplantation* 42:352–358, 1986

I claim:

1. A method of renoprotection in an individual at risk for developing ischemic acute renal failure comprising administering a composition prior to the individual developing ischemic acute renal failure, said composition comprising a therapeutically effective amount of erythropoietin and a pharmaceutically acceptable carrier, for a time and under conditions effective for renoprotection.

2. The method of claim 1 wherein said erythropoietin is recombinant erythropoietin.

3. The method of claim 1 wherein said composition further comprises a member selected from the group consisting of pharmaceutically acceptable solvents, diluents, excipients, emulsifiers, and stabilizers.

4. The method of claim 1 wherein said composition is administered systemically.

5. The method of claim 4 wherein said composition is administered at subpolycythemic doses.

6. The method of claim 5 wherein said subpolycythemic doses are administered 2–4 times over a period of 2–4 days.

7. The method of claim 6 wherein said doses are administered 24 hours apart.

8. The method of claim 5 wherein said doses are in the range of about 250–350 U/kg body weight of erythropoietin in said composition.

9. The method of claim 1 wherein said individual at risk for developing ischemic acute renal failure comprises individuals with diabetes, underlying renal insufficiency, nephritic syndrome, elderly, atherosclerotic disease, nephrotoxic agent recipients, sepsis, hypotensive individuals, hypoxic individuals, pre-surgery, myoglobinuria-hematuria, pregnancy associated acute renal failure, and liver disease.

10. The method of claim 1 wherein said composition is administered up to six hours prior to surgery or administration of nephrotoxic agents.

11. A method of treating ischemic acute renal failure in an individual at risk for developing ischemic acute renal failure comprising administering a composition prior to the individual developing ischemic acute renal failure, said composition comprising a therapeutically effective amount of erythropoietin and a pharmaceutically acceptable carrier, for a time and under conditions effective for renoprotection during ischemic acute renal failure.

12. The method of claim 11 wherein said erythropoietin is recombinant erythropoietin.

13. The method of claim 11 wherein said composition further comprises a member selected from the group consisting of pharmaceutically acceptable solvents, diluents, excipients, emulsifiers, and stabilizers.

14. The method of claim 11 wherein said composition is administered systemically.

15. The method of claim 14 wherein said composition is administered at subpolycythemic doses.

16. The method of claim 15 wherein said subpolycythemic doses are administered 2–4 times over a period of 2–4 days.

17. The method of claim 16 wherein said doses are administered 24 hours apart.

18. The method of claim 16 wherein at least one of said doses is administered prior to development of ischemic acute renal failure and at least one of said doses is administered post-development of ischemic acute renal failure.

19. The method of claim 15 wherein said doses are in the range of about 250–350 U/kg body weight of erythropoietin in said composition.

20. The method of claim 17 wherein said individual at risk for developing ischemic acute renal failure comprises individuals with diabetes, underlying renal insufficiency, nephritic syndrome, elderly, atherosclerotic disease, nephrotoxic agent recipients, sepsis, hypotensive individuals, hypoxic individuals, pre-surgery, myoglobinuria-hematuria, pregnancy associated acute renal failure, and liver disease.

21. The method of claim 11 wherein said composition is administered up to six hours prior to surgery or administration of nephrotoxic agents.

* * * * *